US008668464B2

(12) United States Patent
Kensy et al.

(10) Patent No.: US 8,668,464 B2
(45) Date of Patent: Mar. 11, 2014

(54) METHOD FOR TRANSPORTING A FLUID AND DEVICE FOR PRODUCING A VOLUME FLOW

(75) Inventors: Arnd Kensy, Michendorf (DE); Konrad-Wenzel Winkler, Warin (DE); Andreas Runow, Schwerin (DE); Frank Niklas, Lübz (DE); Gernot Schlee, Schwerin (DE)

(73) Assignee: Human Med AG, Schwerin (DE)

( * ) Notice: Subject to any disclaimer, the term of this patent is extended or adjusted under 35 U.S.C. 154(b) by 447 days.

(21) Appl. No.: 12/964,390

(22) Filed: Dec. 9, 2010

(65) Prior Publication Data

US 2011/0194945 A1 Aug. 11, 2011

(30) Foreign Application Priority Data

Dec. 23, 2009 (DE) .......................... 10 2009 055 227

(51) Int. Cl.
*A61M 1/00* (2006.01)
*F04B 49/00* (2006.01)

(52) U.S. Cl.
USPC .................... 417/53; 417/26; 417/43; 604/30

(58) Field of Classification Search
USPC .............. 417/26, 43, 53; 604/30, 27; 606/167
See application file for complete search history.

(56) References Cited

U.S. PATENT DOCUMENTS

| 3,520,477 | A | 7/1970 | Cooley |
| 5,591,184 | A | 1/1997 | McDonnell et al. |
| 5,735,815 | A | 4/1998 | Bair |
| 6,423,028 | B1 | 7/2002 | Gonon |
| 8,480,698 | B2 * | 7/2013 | Hartwell ....................... 606/167 |
| 2002/0116021 | A1 | 8/2002 | Gordon |
| 2007/0129680 | A1 | 6/2007 | Hagg et al. |
| 2008/0172075 | A1 | 7/2008 | Ammann |
| 2008/0243157 | A1 * | 10/2008 | Klein et al. ................... 606/167 |

FOREIGN PATENT DOCUMENTS

| DE | 699 27 153 T2 | 7/2006 |
| EP | 1 670 371 B1 | 6/2006 |
| WO | 01/97700 A1 | 12/2001 |
| WO | 2004/112623 A2 | 12/2004 |
| WO | 2005/034777 A1 | 4/2005 |

OTHER PUBLICATIONS

European Search Report dated Jul. 17, 2013.

* cited by examiner

*Primary Examiner* — Charles Freay
*Assistant Examiner* — Philip Stimpert
(74) *Attorney, Agent, or Firm* — Norris McLaughlin & Marcus P.A.

(57) ABSTRACT

The invention relates to a method for transporting a fluid for generating a fluid jet, wherein the fluid is delivered from a pump under pressure with a predetermined volume flow to an exit opening. In the event of an interruption of the volume flow, the pump is automatically switched from an operating mode for generating pressure to an operating mode for suctioning fluid; and a device for producing a volume flow for realizing a fluid jet for cutting and/or flushing of material, comprising a pump with an operating mode for generating pressure in the fluid and for generating suction. The device is constructed such that during interruption of the set volume flow, the pumpcan be switched over or switches over automatically from the operating mode for generating pressure to an operating mode for generating suction for the purpose of suctioning fluid.

5 Claims, 1 Drawing Sheet

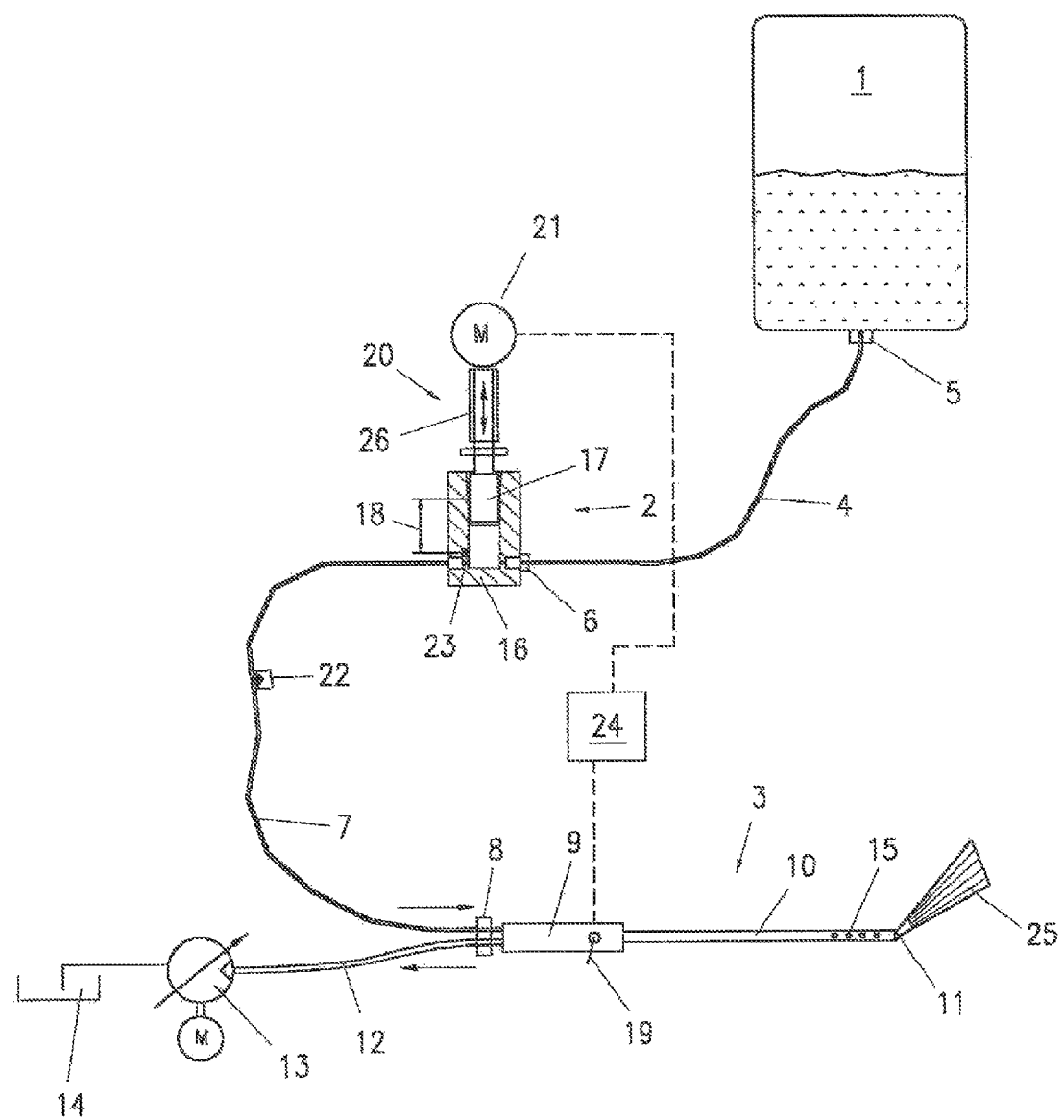

METHOD FOR TRANSPORTING A FLUID AND DEVICE FOR PRODUCING A VOLUME FLOW

This application claims foreign priority benefit under 35 U.S.C. §119 of German application No. 102009055227.8 filed Dec. 23, 2009.

The present invention relates to a method for transporting a fluid for producing a fluid jet, wherein the fluid is delivered from a pump under pressure with a predetermined volume flow to an exit opening.

The present invention also relates to a device for producing a volume flow for realizing a fluid jet for cutting solid or paste-like material, which includes a pump, by which an operating mode for generating pressure in the fluid and an operating mode for generating suction can be realized.

It is known to cut a biological structure with devices having water jets and simultaneously or shortly thereafter suction the biological structure. Such devices are particularly used for liposuction. Such devices include primarily a fluid reservoir and a pump which supplies a fluid under pressure to a tool configured for generating a jet, wherein the fluid is elected as a jet under pressure onto or into a solid body or soft tissue, thereby breaking off segments of this body/tissue. By generating a vacuum proximate to the jet nozzle, the separated segments are suctioned into the tool and delivered to a collection container. Accordingly, suction and also removal of biological structures can be realized minimally invasively. The tools or devices for performing the jet cutting and suctioning are for hygienic reasons frequently designed as single-use devices. The tools or devices should also be lightweight to facilitate manual handling. The entire device must be capable of being operated intuitively and must be constantly ready.

EP 1 670 371 B1 describes the transport device for sterile media which has two piston-cylinder units for generating pressure, with overlapping suction and pressure cycles for generating pressure and simultaneously generating suction, so that the volume flow exiting the jet can be continuously maintained.

Disadvantageously, this transport device has a relatively complex structure for realizing the application-specific volume flow.

WO 2004/112623 A2 discloses a water jet device for separating a biological structure which includes a pump for generating pressure as well as suction and has only a single piston-cylinder unit. The piston of the pump is driven by a cam, wherein upon contact between the piston and the cam at the maximum cam radius, the piston is located at its front dead center and therefore at the end of the movement for generating pressure; conversely, upon contact between the piston and the cam at the minimum radius, the piston is located at the rear dead center and hence at the end of the stroke for generating suction. Depending on the movement direction of the cam, an operating mode for generating pressure or an operating mode for generating suction can be realized.

During the operation of the water jet device and in particular when separating a biological structure, the operator may have to interrupt the jet in order to reposition the tool and/or to perform intermediate operative steps and/or to visually inspect the operating area. This interruption is typically attained by operating an operating device. After termination of the interruption, the volume flow should be redirected with the previously set parameters to the material to be cut.

In the water jet device according to WO 2004/112623 A2, a problem exists when interrupting and resuming the water jet operation, in that the cam is stopped at a certain angular position when the fluid jet is interrupted and rotates again when the jet operation is resumed, so that the cam moves the piston again farther forward to generate pressure. Accordingly, only the fluid volume available which can be held in the cylinder of the piston-cylinder unit for each stroke of the piston is available to the operator for the jet operation. When operating for extended times or when the demand for fluid is greater, the jet operation must therefore be interrupted, allowing the piston to be raised again to the rear dead center during further rotation of the cam and simultaneously generating suction relative to the storage container. The cylinder space can then be filled again with fluid and the pressure in the fluid can be built up for generating a jet while the cam continues to rotate or counter-rotates.

It is therefore an object of the present invention to provide a method and a device by which a certain fluid volume flow can be provided for the longest possible time duration in a simple and cost-effective constructive embodiment for operations having different volume flow requirements.

According to the invention, a method for transporting a fluid for the purpose of generating a fluid jet, wherein the fluid is delivered from a pump under pressure with a predetermined volume flow to an exit opening, wherein in the event of an interruption of the volume flow, the pump is automatically switched from an operating mode for generating pressure to an operating mode for producing suction for the purpose of suctioning fluid. The method can be used to supply a fluid to a surgical or medical instrument, i.e., a device with a fluid jet for the purpose of cutting or flushing a biological structure, such as lipids or tissue, which can be suctioned later or simultaneously. The method can hence be used for weight reduction and/or for reducing the body volume of a patient.

Alternatively, the method may not be employed in medical or surgical treatment of a human or animal body, but may be used, for example, for cleaning for removing structures, optionally biological structures, from surfaces.

The method according to the invention is implemented so that very simple and cost-effectively constructed pumps can be used, wherein these pumps can be operated either only in a pressure operation or only in a suction operation, with the pumps being configured to be switched between pressure and suction. Because the pump in a single use device represents a relatively large cost factor, simple pumps can significantly minimize the manufacturing costs. In spite of the simple and cost-effective structure, the fluid, which in most application is a liquid, can be reliably delivered with the pump to the jet nozzle with a predetermined volume flow of a certain size. An interruption of the volume flow is meant to indicate a decrease of the physical quantity "volume flow" below a certain minimum value within a certain time window. When the volume flow is interrupted, a respective signal is generated by an operating device affecting the set volume flow and/or by a sensor. The sensor may be disposed in the line to the exit opening, at the exit opening itself, or in the drive unit. The sensor on the line or on the outlet opening is capable of detecting the presence or absence of a volume flow. A sensor of a distance measuring system of a linear actuator cylinder, which moves the piston-cylinder unit, can also detect the end position of the piston on its travel to generate the pressure. The signal generated by the corresponding sensor or the distance measuring system is either supplied directly the pump, whereafter the pump switches to the operating mode for generating suction, or the generated signal is transmitted to a control device which sends to the pump a signal causing the switchover.

In an advantageous embodiment of the invention, the volume flow may be delivered to the exit opening pulsating, wherein the time intervals between the individual volume flow segments realizing the pulsation are between 0.05 and 30 seconds.

This means that the set desired volume flow includes intervals, where an interruption of the volume flow caused by the interval does not represent an interruption within the context of the invention. In other words, when the operating mode for generating pressure is interrupted, the pump switches independent of the interval to the operating mode for generating suction. Depending on the set value of the volume flow, a certain desired fluid flow is attained which can have different parameters with respect to the pressure, the frequency and other physical values, wherein a decrease of the value of the physical volume flow over a certain time span below a certain limit value is considered an interruption of the fluid flow, and the pump is switched over according to the invention. When using a control device, the pulse frequencies, intervals and time duration of the operating modes for generating pressure and suction with the control device should be essentially freely adjustable and programmable. If the time intervals between volume flow segments are zero or near zero, then a pulsation-free or essentially pulsation-free volume flow can be produced.

Advantageously, according to the method, a suction operation is performed after the switchover until a signal for terminating the interruption of the volume flow is generated, whereafter the pump is switched back into the operating mode for generating pressure. This signal for terminating the interruption of the volume flow may be generated by an operating device which was previously used for interrupting the volume flow, or the signal may be generated by a sensor measuring an exhaustion of the capacity of the pump is operating mode for generating suction or by another turn-off command terminating the entire process.

Advantageously, the pressure operation may be realized until a signal about the determination of the interruption of the operation with suction is generated, whereafter the pump switches over into the operating mode of the suction operation.

For adapting the method of the invention to the anticipated fluid demand of the user, the time duration of the operating mode for generating pressure and/or the time duration of the operating mode for generating suction are set with a control device before or during the process. The stroke of the piston can then be variably controlled, thereby affecting the fluid volume available in a time window at a certain pressure, in particular with a steady output of a motor drive of the pump.

Advantageously, the time duration for the operating mode for generating suction is shorter than the time duration for the operating mode for generating pressure. The maximum fluid volume can then be provided again to the user within a shorter time span than the duration of the jet.

When using a piston pump, the control device may control the piston stroke such that the piston stroke in the operating mode generating suction is shorter, identical or longer than the piston stroke performed in the previously realized operating mode for generating pressure. However, the configuration of the stroke can generally be performed only in a single pressure-suction cycle.

This method of the invention ensures that during interruption of the volume flow the time window of the interruption is used to fill the space available in the piston-cylinder unit again with fluid by switching the pump over into the operating mode for generating suction, so that the maximum fluid volume is again available when the interruption ends.

The method is performed independent of the respective piston position. In jet cutting, in particular in medical or surgical interventions, the operator typically interrupts the jet process for evaluating the obtained result. The invention then ensures that fluid for jet operation is available over a long and only interrupted time interval as a result of the suction effect realized during the interruption phase.

For carrying out the method, a device for producing a volume flow for the purpose of realizing a fluid jets for cutting or flushing a solid material or soft tissue is provided, wherein the device includes a pump configured to realize an operating mode for generating pressure in the fluid and an operating mode for generating suction. According to the invention, the device is constructed such that during interruption of the set volume flow, the pump can be switched or switches automatically from the operating mode for generating pressure to an operating mode for generating suction for the purpose of suctioning fluid. The device advantageously includes a control device which controls or triggers the switchover of the pump. The solid or soft material which is cut or flushed out with the fluid jet, can be biological tissue (e.g., lipids), so that the device is suitable for cutting or flushing and subsequent or simultaneous liposuction. A volume flow is produced with the pump of the device in a line included in the device and arranged downstream in the direction of the volume flow and delivered through an exit opening, e.g., in form of a nozzle. When the volume flow in the line is interrupted, the pump is automatically switched over according to the invention into the operating mode for generating suction.

To minimize the manufacturing costs of the device, the pump includes a piston pump with only a single piston-cylinder unit. In other words, the pump has only a single pump chamber capable of generating a sufficiently long, statically constant or increasing or pulsating fluid jet, wherein interruptions of the pressure phase in the application, for example in a surgical or medical operation, are used to fill the chamber as quickly as possible with fluid by switching over to the operating mode for generating suction.

For driving the piston of the piston pump, the piston may be movable with a motor-operated spindle drive or a linear actuator cylinder. In other words, through coupling with a spindle, which cooperates with a nut coupled to a motor drive unit, the spindle and hence also the piston can be moved in a translatory fashion. Alternatively, the spindle itself may be coupled to a motor drive unit with the nut arranged on the spindle and transmitting the translatory motion to the piston.

In a particular embodiment, the piston pump may be motor driven and the device may include a gear which makes it possible to move, with an identical rotation speed of the motor drive, the piston in the operating mode for generating suction with greater speed than when moving the piston in the operating mode for generating pressure. In another preferred embodiment, the motor drive may be designed so as to generate in the operating mode for generating suction when only a small load is applied, a correspondingly higher rotation speed than in the operating mode for generating pressure with a higher load.

To simplify the operation of the device, the device may include an operating device configured to manually interrupt the volume flow. Manual operation of the operating unit may also include a foot switch, wherein an important feature of the operating device is it can be directly operated by an operator.

The operating device may be configured so as to generate upon operation for interrupting the volume flow a signal about the interruption of the volume flow. In other words, by operating the operating device, the pump may be switched over or a signal about the interruption of the volume flow may be generated which may then be transmitted to a control device which is part of the device. The control device controls the pump so as to cause the pump to switch over. In an alternative embodiment, the operating device interrupts the volume flow at least when operated for the first time and simultaneously switches the pump over mechanically. In another embodiment of the device, the device may, when the operating device is operated again, cause the pump to switch back to the operating mode for generating pressure.

For determining an interruption in the volume flow, the device may include a first sensor arranged in a line downstream of the pump in the flow direction of the volume flow and configured for measuring an interruption of the volume flow. Alternatively, the first sensor may also be arranged outside the line, but proximate to the exit opening. The sensor can generate a signal about the interruption when measuring the interruption of the volume flow, with the signal being transmitted to the control device which controls the pump and causing the pump to switch over.

Alternatively in addition, the device may include a distance measuring system disposed on the piston pump or drive unit, with which the position of the piston in any position during the operating mode for generating pressure and hence interruptions of the volume flow can be detected. This distance measuring system can detect the position of the piston in the front dead center and can hence also detect the interruption of the volume flow and then generate a signal about the interruption of the volume flow which is transmitted to the control device which is part of the device and controls the pump so that the pump switches over. In other words, in the event that the pump chamber becomes completely empty of at this time, the pump chamber is forcibly filled within a short time by initiating the operating mode for generating suction. (The distance measuring system is a distance measurement in the drive unit/actuator cylinder which identifies the position of the pressure rod=piston).

Advantageously, the device includes the aforementioned control device, which is configured for setting the volume flow intervals to be generated and/or the temporal separation between the volume flow intervals and/or the time duration for the two operating modes for generating suction and pressure. This means that the control device is programmable so that the volume flow controlled by the control device can be set with predetermined desired parameters. The set or settable volume flow can here be a constant volume flow, an increasing volume flow or a pulsating volume flow. The control device can also be used to transmit signals to the pump about the interruption and/or the cancellation or termination of the interruption or can generate corresponding controls signals and transmit these control signals to the pump for causing switchover.

The device of the invention is therefore constructed to provide to a user a maximum fluid volume for producing a jet over a long and optionally interrupted time span, wherein the device has a simpler structure and hence reduced manufacturing and material requirements and a low weight.

The invention will now be described with reference to the appended drawing.

The sole FIG. 1 shows a device according to the invention for carrying out the method according to the invention for transporting a fluid.

The device according to the invention is essentially composed of three main components: namely a reservoir 1, a pump 2 and an operating tool 3. Fluid is supplied from the reservoir 1 to the pump 3 which transports the fluid at higher pressure to the operating tool 3, from which the fluid exits as a fluid jet 25.

The reservoir 1 and the pump 2, which is constructed as a piston-cylinder unit, are connected with each other via a suction line 4, wherein the suction line 4 is connected by way of a first coupling 5 with the reservoir 1 and by way of a second coupling 6 with the pump 2. The pump 2 is also connected with the operating tool 3 via a pressure line 7, wherein the connection with the operating tool 3 is realized by way of a third coupling 8. The operating tool 3 includes a hand piece 9 and a pressure and suction tube 10. The pressure and suction tube 10 includes an interior pressure cannula with an exit opening 11 located at an end which is connected to the pressure line 7 extending to the operating tool 3. The suction line 10 is connected with a receiving tank 14 by way of a suction line 12 and a suction pump 13. The suction tube 10 also includes along its periphery radially extending suction openings 15 for receiving the separated segments and the collected separation fluid.

The pump 2 includes a cylinder 16 in which a piston 17 can move with a translatory motion along its piston stroke 18. The translatory motion of the piston 17 is driven by a connected spindle drive 20 which is powered by a drive unit 21, preferably an electric motor. The actual structure of the spindle drive will not be described in detail.

Instead of the spindle drive, a linear actuator cylinder can be used which is operatively connected with the piston by a plug-in coupling. The linear actuator cylinder includes, for example, a planetary roller screw and an AC servo motor. The structure and operation are known and will not be explained here in detail.

The invention also includes a control device 24 which is connected at least with the drive unit 21 so as to be able to affect its rotation. When the drive unit 21 is operated, the spindle drive 20 or the linear actuator cylinder is operated such that the piston 17 is moved in a translatory fashion. When the piston 17 moves to the front (in the illustration downward), the pressure in the fluid that resides in the cylinder 16 increases. By arranging an unillustrated check valve in the suction line 4, the fluid is urged to flow to the operating tool 3 and exit from the pressure and suction tube 10 as a fluid jet 25.

When the fluid jet 25 is interrupted by operating an operating device 19 on the hand piece 9 (or in an unillustrated manner by a foot switch), a signal about the interruption is generated and the drive unit 25 is controlled by the control device 24 so as to reverse its rotation direction and hence move the piston 17 by way of the spindle drive 20 or the linear actuator cylinder rearward (in the illustration upward). This causes the pump 2 to produce a suction effect, causing additional fluid to flow from the reservoir 1 into the cylinder 16. This additional fluid then becomes available for generating the fluid jet 25 when the movement direction of the piston 17 is reversed again. The fluid jet 25 can not only be interrupted by a signal based on the operation of the operating device 19, by can alternatively or in addition also be generated by a sensor 22 on the pressure line 7 or by a sensor at the position 23 which determines when the piston 17 reaches its end position during its travel in the operating mode for generating pressure.

A distance measuring system 26 for detecting the movement of the piston 17 can also be provided. This distance measuring system 26 cooperates with the spindle drive 20 or the linear actuator cylinder.

It is evident that in spite of the simple construction of the piston 17, the piston 17 is capable of using the time window provided by the interruption for filling the cylinder 16 again based on the control of its movement according to the invention when the fluid jet 25 is interrupted. Consequently, a larger fluid volume for operating the jet is available at the termination of the interruption than would be possible with conventional devices.

The switchover to the operating mode for generating suction is automatic, so that the user, in particular when performing a medical or surgical operation, does not have to be mindful of refilling the cylinder 16 and need only operate the operating device 19 again for the purpose of terminating the interruption of the volume flow. If suction is generated automatically based on the control of the second sensor/distance measuring system 23, without operation of the operating device 19 by the user, then a switchover into the operating mode for generating pressure occurs automatically when the piston reaches the rear end position. The device according to the invention is therefore particularly useful as a cost-effective and lightweight single use device for liposuction.

LIST OF REFERENCES SYMBOLS

1 Reservoir
2 Pump
3 Operating tool
4 Suction line
5 First coupling
6 Second coupling
7 Pressure line
8 Third coupling
9 Hand piece
10 Pressure and suction tube with interior pressure line
11 Exit opening
12 Suction line
13 Suction pump
14 Receiving tank
15 Suction opening
16 Cylinder
17 Piston
18 Piston stroke
19 Operating device
20 Spindle drive
21 Drive unit
22 Sensor
23 Sensor
24 Control device
25 Fluid jet
26 Distance measuring system

The invention claimed is:

1. Method for transporting a fluid for the purpose of generating a fluid jet (25), wherein the fluid is delivered from a pump (2) under pressure with a predetermined volume flow to an exit opening (11), wherein in the event of an interruption of the volume flow, the pump (2) is automatically switched from an operating mode for generating pressure to an operating mode for generating suction for the purpose of suctioning fluid, such that the operating mode for generating suction is realized until a signal for terminating the interruption of the volume flow is generated, whereafter the pump (2) is switched over to the operating mode for generating pressure, and the operating mode for generating pressure is realized until a signal for terminating interruption of the suction operation is generated, whereafter the pump (2) switches over to the operating mode for generating suction.

2. Method for transporting a fluid according to claim 1, wherein
the volume flow is delivered to the exit opening (11) without pulsation or while pulsating, wherein the time intervals between the individual volume flow segments realizing the pulsation are between 0.05 and 30 seconds.

3. Method for transporting a fluid according to claim 1, wherein
the time duration of the operating mode for generating pressure and/or the time duration of the operating mode for generating suction is set with a control device (24) before or during the process.

4. Method for transporting a fluid for the purpose of generating a fluid jet (25), wherein the fluid is delivered from a pump (2) comprising a pump and a cylinder, under pressure with a predetermined volume flow to an exit opening (11),
wherein in the event of an interruption of the volume flow, the pump (2) is automatically switched from an operating mode for generating pressure to an operating mode for generating suction for the purpose of suctioning fluid,
wherein the time duration of the operating mode for generating pressure and/or the time duration of the operating mode for generating suction is set with a control device (24) before or during the process, and
the time duration of the operating mode for generating suction compared to the time duration for the operating mode for generating pressure is dependent upon a position of the piston (17) in the cylinder (16) at the time the signal for switching into the operating mode for generating suction is generated.

5. Method for transporting a fluid for the purpose of generating a fluid jet (25), wherein the fluid is delivered from a pump (2) comprising a piston and a cylinder, under pressure with a predetermined volume flow to an exit opening (11),
wherein in the event of an interruption of the volume flow, the pump (2) is automatically switched from an operating mode for generating pressure to an operating mode for generating suction for the purpose of suctioning fluid, wherein
when using the pump, a control device (24) controls a piston stroke (18) during the operating mode for generating suction with respect to the piston stroke (18) performed in the previously realized operating mode for generating pressure.

* * * * *